(12) United States Patent
Ahn et al.

(10) Patent No.: US 8,541,378 B2
(45) Date of Patent: Sep. 24, 2013

(54) RECOMBINANT ALBUMINS FUSED WITH POLY-CYSTEINE PEPTIDE AND THE METHODS FOR PREPARING THE SAME

(75) Inventors: Hyung Jun Ahn, Seoul (KR); Ick Chan Kwon, Seoul (KR); Kuiwon Choi, Seoul (KR); Kwangmyeng Kim, Seoul (KR); Inchan Youn, Seoul (KR); Sehoon Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 467 days.

(21) Appl. No.: 12/792,186

(22) Filed: Jun. 2, 2010

(65) Prior Publication Data

US 2010/0310468 A1 Dec. 9, 2010

(30) Foreign Application Priority Data

Jun. 5, 2009 (KR) .................. 10-2009-0049866

(51) Int. Cl.
*A61K 38/10* (2006.01)
(52) U.S. Cl.
USPC ...................... 514/21.4; 514/21.2; 514/1.1
(58) Field of Classification Search
None
See application file for complete search history.

(56) References Cited

U.S. PATENT DOCUMENTS

| 6,339,062 B1 * | 1/2002 | Williams et al. | 514/13.3 |
| 6,692,790 B2 * | 2/2004 | Liu et al. | 427/2.26 |
| 2005/0170070 A1 * | 8/2005 | Layrolle et al. | 427/2.1 |

FOREIGN PATENT DOCUMENTS

| KR | 1020050083933 A | 8/2005 |
| WO | 2004/045640 A1 | 6/2004 |

OTHER PUBLICATIONS

Kang et al., Cellular Delivery and Biological Activity of Antisense Oligonucleotides Conjugated to a Targeted Protein Carrier, Bioconjugate Chem., vol. 19 p. 2182-2188 (Oct. 1, 2008).*
Gradishar, et al., "Phase III Trial of Nanoparticle Albumin-Bound Paclitaxel Compared With Polyethylated Castor Oil-Based Paclitaxel in Women With Breast Cancer.", Journal of Clinical Oncology, 23:7794-7803, 2005.
Chuang, et al., "Pharmaceutical Strategies Utilizing Recombinant Human Serum Albumin.", Pharmaceutical Research,19:569-577, 2002.
Kratz, "Albumin as a drug carrier: Design of prodrugs, drug conjugates and nanoparticles.", Journal of Controlled Release, 132:171-183, 2008.
Hyunmin Kang, et al; "Cellular Delivery and Biological Activity of Antisense Oligonucleotides Conjugated to a Targeted Protein Carrier", Bioconjugate Chem., vol. 19, pp. 2182-2188, Published on Web Oct. 1, 2008.
KIPO NFOA Appln. No. 10-2009-0049866; dated Dec. 17, 2012.

* cited by examiner

*Primary Examiner* — Cecilia J Tsang
*Assistant Examiner* — Randall L Beane
(74) *Attorney, Agent, or Firm* — Ladas & Parry LLP

(57) ABSTRACT

The present invention relates to recombinant albumins fused with poly-cysteine peptide and methods for preparing the same, more precisely recombinant albumins in which cysteines that can be used for drug binding are amplified at N-terminal and C-terminal of the albumin and methods for preparing the same. The recombinant albumin of the present invention demonstrates improved albumin-drug conjugation efficiency when it is used for drug delivery system, indicating that it can effectively deliver a large amount of drug to a target tissue. At the same time, the recombinant albumin of the present invention can be used as an excellent drug deliverer with reduced side effects, compared with the conventional albumin carriers, by regulating the amount of drug conjugated to each unit of albumin by regulating the number of cysteine fused thereto. In addition, the recombinant albumin of the present invention can be used for the screening of a novel drug and for the non-invasive real-time diagnosis and treatment of disease by combining with a fluorescent material or a contrast agent for molecular imaging.

12 Claims, 7 Drawing Sheets

Human serum albumin: 67.2kDa

FIG. 6

SEQUENCE LISTING

```
<160> NUMBER OF SEQ ID NOS: 6

<210> SEQ ID NO 1
<211> LENGTH: 20
<212> TYPE: PRT
<213> ORGANISM: Artificial Sequence
<220> FEATURE:
<223> OTHER INFORMATION: poly-cysteine peptide 1

<400> SEQUENCE: 1

Cys Gly Cys Gly Cys Gly Cys Gly Cys Gly Cys Gly Cys Gly Cys Gly
1               5                   10                  15

Cys Gly Cys Gly
            20

<210> SEQ ID NO 2
<211> LENGTH: 10
<212> TYPE: PRT
<213> ORGANISM: Artificial Sequence
<220> FEATURE:
<223> OTHER INFORMATION: poly-cysteine peptide

<400> SEQUENCE: 2

Cys Ser Cys Ser Cys Ser Cys Ser Cys Ser
1               5                   10
```

<210> SEQ ID NO 3
<211> LENGTH: 8
<212> TYPE: PRT
<213> ORGANISM: Artificial Sequence
<220> FEATURE:
<223> OTHER INFORMATION: linker peptide

<400> SEQUENCE: 3

```
Gly Ser Gly Ala Gly Ser Gly Ala
1               5
```

<210> SEQ ID NO 4
<211> LENGTH: 618
<212> TYPE: PRT
<213> ORGANISM: Artificial Sequence
<220> FEATURE:
<223> OTHER INFORMATION: Recombinant albumin fused with poly-cysteine
      peptide

<400> SEQUENCE: 4

```
Tyr Val Arg Gly Asp Gly Ala Ser Ala Gly Ser Gly Glu Phe Cys Gly
1               5                   10                  15

Cys Gly Cys Gly Cys Gly Cys Gly Cys Gly Cys Gly Cys Gly Cys Gly
                20                  25                  30

Cys Asp Ala His Lys Ser Glu Val Ala His Arg Phe Lys Asp Leu Gly
            35                  40                  45

Glu Glu Asn Phe Lys Ala Leu Val Leu Ile Ala Phe Ala Gln Tyr Leu
        50                  55                  60

Gln Gln Cys Pro Phe Glu Asp His Val Lys Leu Val Asn Glu Val Thr
65                  70                  75                  80

Glu Phe Ala Lys Thr Cys Val Ala Asp Glu Ser Ala Glu Asn Cys Asp
                85                  90                  95

Lys Ser Leu His Thr Leu Phe Gly Asp Lys Leu Cys Thr Val Ala Thr
            100                 105                 110

Leu Arg Glu Thr Tyr Gly Glu Met Ala Asp Cys Cys Ala Lys Gln Glu
        115                 120                 125

Pro Glu Arg Asn Glu Cys Phe Leu Gln His Lys Asp Asp Asn Pro Asn
130                 135                 140

Leu Pro Arg Leu Val Arg Pro Glu Val Asp Val Met Cys Thr Ala Phe
145                 150                 155                 160

His Asp Asn Glu Glu Thr Phe Leu Lys Lys Tyr Leu Tyr Glu Ile Ala
                165                 170                 175

Arg Arg His Pro Tyr Phe Tyr Ala Pro Glu Leu Leu Phe Phe Ala Lys
            180                 185                 190

Arg Tyr Lys Ala Ala Phe Thr Glu Cys Cys Gln Ala Ala Asp Lys Ala
        195                 200                 205

Ala Cys Leu Leu Pro Lys Leu Asp Glu Leu Arg Asp Glu Gly Lys Ala
210                 215                 220

Ser Ser Ala Lys Gln Arg Leu Lys Cys Ala Ser Leu Gln Lys Phe Gly
225                 230                 235                 240

Glu Arg Ala Phe Lys Ala Trp Ala Val Ala Arg Leu Ser Gln Arg Phe
                245                 250                 255

Pro Lys Ala Glu Phe Ala Glu Val Ser Lys Leu Val Thr Asp Leu Thr
            260                 265                 270

Lys Val His Thr Glu Cys Cys His Gly Asp Leu Leu Glu Cys Ala Asp
        275                 280                 285

Asp Arg Ala Asp Leu Ala Lys Tyr Ile Cys Glu Asn Gln Asp Ser Ile
290                 295                 300
```

```
Ser Ser Lys Leu Lys Glu Cys Cys Glu Lys Pro Leu Leu Glu Lys Ser
305                 310                 315                 320

His Cys Ile Ala Glu Val Glu Asn Asp Glu Met Pro Ala Asp Leu Pro
            325                 330                 335

Ser Leu Ala Ala Asp Phe Val Glu Ser Lys Asp Val Cys Lys Asn Tyr
        340                 345                 350

Ala Glu Ala Lys Asp Val Phe Leu Gly Met Phe Leu Tyr Glu Tyr Ala
    355                 360                 365

Arg Arg His Pro Asp Tyr Ser Val Val Leu Leu Arg Leu Ala Lys
370                 375                 380

Thr Tyr Glu Thr Thr Leu Glu Lys Cys Cys Ala Ala Ala Asp Pro His
385                 390                 395                 400

Glu Cys Tyr Ala Lys Val Phe Asp Glu Phe Lys Pro Leu Val Glu Glu
                405                 410                 415

Pro Gln Asn Leu Ile Lys Gln Asn Cys Glu Leu Phe Glu Gln Leu Gly
            420                 425                 430

Glu Tyr Lys Phe Gln Asn Ala Leu Leu Val Arg Tyr Thr Lys Lys Val
        435                 440                 445

Pro Gln Val Ser Thr Pro Thr Leu Val Glu Val Ser Arg Asn Leu Gly
    450                 455                 460

Lys Val Gly Ser Lys Cys Cys Lys His Pro Glu Ala Lys Arg Met Pro
465                 470                 475                 480

Cys Ala Glu Asp Tyr Leu Ser Val Val Leu Asn Gln Leu Cys Val Leu
                485                 490                 495

His Glu Lys Thr Pro Val Ser Asp Arg Val Thr Lys Cys Cys Thr Glu
            500                 505                 510

Ser Leu Val Asn Arg Arg Pro Cys Phe Ser Ala Leu Glu Val Asp Glu
        515                 520                 525

Thr Tyr Val Pro Lys Glu Phe Asn Ala Glu Thr Phe Thr Phe His Ala
    530                 535                 540

Asp Ile Cys Thr Leu Ser Glu Lys Glu Arg Gln Ile Lys Lys Gln Thr
545                 550                 555                 560

Ala Leu Val Glu Leu Val Lys His Lys Pro Lys Ala Thr Lys Glu Gln
                565                 570                 575

Leu Lys Ala Val Met Asp Asp Phe Ala Ala Phe Val Glu Lys Cys Cys
            580                 585                 590

Lys Ala Asp Asp Lys Glu Thr Cys Phe Ala Glu Glu Gly Lys Lys Leu
        595                 600                 605

Val Ala Ala Ser Gln Ala Ala Leu Gly Leu
    610                 615

<210> SEQ ID NO 5
<211> LENGTH: 585
<212> TYPE: PRT
<213> ORGANISM: Homo sapiens

<400> SEQUENCE: 5

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60
```

```
Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
        130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
```

```
                    485                 490                 495
Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 6
<211> LENGTH: 1857
<212> TYPE: DNA
<213> ORGANISM: Artificial Sequence
<220> FEATURE:
<223> OTHER INFORMATION: Polynucleotide encoding recombinant albumin
      fused with poly-cysteine peptide

<400> SEQUENCE: 6
tacgtaagag gtgatggtgc ttctgctggt tctggtgaat ctgtggatg  tggttgtggt      60 tgtggatgtg gttgtggatg tggttgtgga tgtggttgtg atgcacacaa gagtgaggtt     120
gctcatcggt ttaaagattt gggagaagaa aatttcaaag ccttggtgtt gattgccttt     180
gctcagtatc ttcagcagtg tccatttgaa gatcatgtaa aattagtgaa tgaagtaact     240
gaatttgcaa aaacatgtgt tgctgatgag tcagctgaaa attgtgacaa atcacttcat     300 acccttttg gagacaaatt atgcacagtt gcaactcttc gtgaaaccta tggtgaaatg     360
gctgactgct gtgcaaaaca agaacctgag agaaatgaat gcttcttgca acacaaagat     420
gacaacccaa acctcccccg attggtgaga ccagaggttg atgtgatgtg cactgctttt     480
catgacaatg aagagacatt tttgaaaaaa tacttatatg aaattgccag aagacatcct     540 tactttt atg ccccggaact ccttttcttt gctaaaaggt ataaagctgc ttttacagaa     600
tgttgccaag ctgctgataa agctgcctgc ctgttgccaa agctcgatga acttcgggat     660
gaagggaagg cttcgtctgc caaacagaga ctcaagtgtg ccagtctcca aaaatttgga     720
gaaagagctt tcaaagcatg gcagtagct cgtctgagcc agagatttcc caaagctgag     780
tttgcagaag tttccaagtt agtgacagat cttaccaaag tccacacgga atgctgccat     840
ggagatctgc ttgaatgtgc tgatgacagg gcggaccttg ccaagtatat ctgtgaaaat     900
caagattcga tctccagtaa actgaaggaa tgctgtgaaa aacctctgtt ggaaaaatcc     960
cactgcattg ccgaagtgga aaatgatgag atgcctgctg acttgccttc attagctgct    1020
gattttgttg aaagtaagga tgtttgcaaa aactatgctg aggcaaagga tgtcttcctg    1080
ggcatgtttt tgtatgaata tgcaagaagg catcctgatt actctgtcgt gctgctgctg    1140
agacttgcca agacatatga aaccactcta gagaagtgct gtgccgctgc agatcctcat    1200
gaatgctatg ccaaagtgtt cgatgaattt aaacctcttg tggaagagcc tcagaattta    1260
atcaaacaaa attgtgagct ttttgagcag cttggagagt acaaattcca gaatgcgcta    1320
ttagttcgtt acaccaagaa agtacccca  gtgtcaactc caactcttgt agaggtctca    1380
agaaacctag gaaaagtggg cagcaaatgt tgtaaacatc ctgaagcaaa agatatgccc    1440
tgtgcagaag actatctatc cgtggtcctg aaccagttat gtgtgttgca tgagaaaacg    1500
```

```
ccagtaagtg acagagtcac caaatgctgc acagaatcct tggtgaacag gcgaccatgc   1560
ttttcagctc tggaagtcga tgaaacatac gttcccaaag agtttaatgc tgaaacattc   1620
accttccatg cagatatatg cacactttct gagaaggaga gacaaatcaa gaaacaaact   1680
gcacttgttg agctcgtgaa acacaagccc aaggcaacaa aagagcaact gaaagctgtt   1740
atggatgatt tcgcagcttt tgtagagaag tgctgcaagg ctgacgataa ggagacctgc   1800
tttgccgagg agggtaaaaa acttgttgct gcaagtcaag ctgccttagg cttataa     1857
```

RECOMBINANT ALBUMINS FUSED WITH POLY-CYSTEINE PEPTIDE AND THE METHODS FOR PREPARING THE SAME

CROSS-REFERENCES TO RELATED APPLICATION

This patent application claims the benefit of priority under 35 U.S.C §119 of Korean Patent Application No. 10-2009-0049866 filed on Jun. 5, 2009, the contents of which are incorporated herein by reference.

BACKGROUND OF THE INVENTION

1. Field of the Invention

The present invention relates to recombinant albumins fused with poly-cysteine peptide and methods for preparing the same.

2. Description of the Related Art

The usability of albumin, as an effective drug in vivo, has been widely known. In particular, in relation to such disease as cancer and rheumatoid arthritis, albumin has been well recognized in its functions as a multi-drug deliverer because of its capability and easiness in improving physical and chemical characteristics such as high accumulation in a target tissue, low invasiveness in a normal tissue, low toxicity, easiness in conjugation with variety of drugs, drug-release in a target tissue, advantageous bio-degradation time, solubility of the fused drug, etc.

In cancer tissues, albumin is preferably metabolized to produce nitrogen and energy. In angiogenetic blood vessels of cancer tissues, EPR effect (enhanced permeability and retention effect) is observed, that is albumin is accumulated selectively in cancer tissues owing to the increased permeability. Abnormality of lymphatic system in cancer tissues accelerates the accumulation of albumin in cancer tissues. So, drug delivery by albumin is an important target of new drug development, which draws our attention world widely.

Chemotherapy, one of the conventional methods treating cancer, is limited in clinical application because of biophysicochemical properties of a drug used. That is, if it is a hydrophobic drug insoluble in water, a drug deliverer has to be prepared with an organic solvent such as polyethoxylated castor oil (CrEL) or polysorbate 80. In that case, not only the drug itself but also the drug deliverer can cause toxicity, which can cause hypersensitivity and other serious neuronal disease. Therefore, an additional medical treatment is required to control such toxicity. That is, when a drug deliverer depends on such organic solvent, there might be a problem of dose-limiting because of toxicity of the drug deliverer. Precisely, dose of a drug for in vivo injection can be limited.

In in vivo drug delivery, in vivo biostability of a drug is also an important factor. Therefore, biostability and half-life can be regulated by the choice of an efficient drug deliverer.

To reduce the toxicity of a drug deliverer and to improve in vivo biostability of the drug itself, it has been continuously attempted to use albumin protein as a drug deliverer.

As an attempt to reduce toxicity of a drug deliverer, methotrexate-albumin conjugate, albumin-binding prodrug of doxorubicin (DOXO-EMCH), and paclitaxel albumin-stabilized nanoparticle formulation (brand name "Abraxane™") have been clinically tested and acknowledged as effective albumin based drug deliverers.

Abraxane has been approved by FDA, USA, in January, 2005, targeting metastatic breast cancer recurrent patients. It demonstrated excellent capability of drug delivery using albumin. American Bioscience Inc. has developed nab-technology, which is the technology to produce nanoparticles based on albumin, resulting in the success of enveloping a lipid-soluble drug in a nanoparticle. To form albumin nanoparticles in the size of 100-200 nm, a target drug is added to albumin in aqueous solution and then jet stream is blown through under the high pressure. By this method, the anticancer agent Paclitaxel is sealed in nano particles, resulting in the product named Abraxane™ which is clinically treated to metastatic breast cancer patients. Compared with the single-treatment of Paclitaxel, the treatment of Abraxane™ demonstrated less side effects such as decrease of leucocytes, mental and body weakness, infection, and muscle ache and the progress of disease was also retarded by the treatment.

The treatment of Methotrexate known as the agent effective in rheumatoid arthritis is based on the mechanism that albumin is over-accumulated in the region of rheumatoid arthritis and metabolized therein. In an animal model, when Methotrexate/albumin deliverer was administered, treatment effect was improved, compared with when Methotrexate alone was treated.

As a method to improve biostability of a drug itself, the drug is conjugated with albumin to improve pharmacokinetic profile. For example, there are Albumin Fusion Technology (Human Genome Sciences), Drug Affinity Complex (DAM™, ConjuChem. Inc.), Performed Conjugated-Drug Affinity complex technology platform (PC-DAM™, ConjuChem. Inc.) and the method provided by Novo Nordisk to conjugate a fatty acid derivative physically to albumin circulating in human body.

Albumin fusion technology provided by Human Genome Sciences is that albumin is conjugated with cytokine protein such as interferon or interleukin by using genetic recombination technique. In this case, protein pegylation like effect is observed along with increase of in vivo half-life, decrease of degradation by protease, and decrease of immune response.

ConjuChem. Inc. has the technique that is able to conjugate a drug with the $34^{th}$ cysteine free from disulfide bond in albumin by using a reaction group such as N-hydroxysuccinimide ester, isocyanate, maleimide or salicylate group. The company has been conjugated various peptide drugs with albumin by the said method. As an example, CJC-1134-PC, an exendin-4 albumin complex, has been developed as a therapeutic agent for type II diabetes.

Concerning the said drug delivery system, methods of drug conjugation with albumin are largely divided into two categories; which are the method using the $34^{th}$ cysteine residue and the method using lysine residues on the surface of albumin.

In all the commercial albumins, the $34^{th}$ cysteine residue of albumin is blocked by sulfhydryl compound such as cysteine, homocysteine and glutathione. So, only 20-60% of the $34^{th}$ residue can be conjugated with a drug. Therefore, for the effective drug conjugation, it is important to free the $34^{th}$ cysteine from blocking in commercial albumin.

A method to produce a prodrug has been attempted by targeting the $34^{th}$ cysteine residue of albumin circulating in vivo. (4-maleimidophenylacetyl) hydrazone derivative and (6-maleimidophenylacetyl) hydrazone derivative of doxorubicin (DOXO-EMCH) are conjugated with the $34^{th}$ cysteine residue of albumin circulating in vivo within just a few minutes. In that case, the albumin conjugate DOXO-EMCH demonstrates the maximum tolerated dose 4.5 times as high as that of doxorubicin itself that is the albumin conjugate is much effective in treatment than doxorubicin single treatment.

However, even in the case that a drug is conjugated with albumin circulating in vivo, drug binding efficiency is still not high enough because about 70% of those circulating albumin contain free 34<sup>th</sup> cysteine residue, which is in the form of mercaptalbumin opened for drug conjugation.

Methotrexate-albumin conjugate (MTX-HSA) evaluated until clinical test stage I/II is the example of the second method using lysine residues on the surface of albumin for drug conjugation. This conjugate is produced by direct binding of methotrexate with lysine residue of albumin. However, this methotrexate-albumin conjugate has a problem in identification of the conjugate chemically because of irregularity of numbers of drugs being able to be combined with albumin. Clinical evaluation of the methotrexate-albumin conjugate, a kind of prodrug, is postponed because of its uncertainty in cleavage rate and cleavage product.

According to the method using lysine residue on the surface of albumin, the number of drugs that are conjugated with each albumin is not consistent, so that the albumin-drug conjugate cannot be chemically identified and at the same time the number of drugs conjugated thereto cannot be controlled.

Therefore, to overcome the said disadvantages of the conventional albumin-drug conjugation methods, more effective or improved methods for albumin-drug conjugation, for increasing the number of drugs conjugated to each albumin and for regulating the number of drugs conjugated to each albumin are required.

The present inventors have studied to overcome side effects of the conventional drug delivery system using albumin. As a result, the inventors developed a recombinant albumin by combining albumin with poly-cysteine peptide harboring multi-drug binding sites based on genetic recombination technique. The developed recombinant albumin has the increased number of cysteines that can be useful for drug binding at N-terminal and C-terminal along with the 34$^{th}$ residue, so that it not only improves albumin-drug conjugation efficiency for more effective delivery of a large amount of drugs to a target tissue but also facilitates regulation of the number of fused cysteines to control the number of drugs conjugated to each albumin, indicating that this novel recombinant albumin can be used as an excellent drug deliverer with less side effects than the conventional albumin deliverers. Further, the present inventors completed this invention by confirming that the recombinant albumin developed by the inventors can be effectively used for the non-invasive real-time diagnosis and treatment of disease by combining with a fluorescent material or a contrast agent for molecular imaging.

SUMMARY OF THE INVENTION

It is an object of the present invention to provide a recombinant albumin that can deliver a large amount of drugs effectively to a target tissue and facilitate the regulation of the number of drugs conjugated with each unit albumin, methods for non-invasive diagnosis for real-time molecular imaging and treatment of disease, and a composition for the diagnosis.

To achieve the above object, the present invention provides a recombinant albumin fused with poly-cysteine peptide.

The present invention also provides a recombinant albumin-drug conjugate produced by combining a drug with the said recombinant albumin.

The present invention further provides a pharmaceutical composition comprising the said recombinant albumin-drug conjugate.

The present invention also provides a recombinant albumin-fluorescent material conjugate for molecular imaging produced by combining a fluorescent material for molecular imaging with the said recombinant albumin.

The present invention also provides a composition for disease diagnosis comprising the said recombinant albumin-fluorescent material for molecular imaging.

The present invention provides a polynucleotide encoding the said recombinant albumin, an expression vector introduced with the said polynucleotide and a transformant transfected with the said expression vector.

The present invention also provides a method for preparing the said recombinant albumin comprising the following steps:
1) constructing the said expression vector;
2) preparing the said transformant by transfecting a host cell with the expression vector constructed in step 1); and
3) obtaining the recombinant albumin fused with poly-cysteine peptide from the transformant prepared in step 2).

The present invention also provides a method for preparing a recombinant albumin-drug conjugate containing the additional step of obtaining a recombinant albumin-drug conjugate by combining a drug with the recombinant albumin obtained in step 3) (step 4).

The present invention also provides a method for preparing a recombinant albumin-fluorescent material conjugate for molecular imaging comprising the additional step of obtaining a recombinant albumin-fluorescent material conjugate for molecular imaging by combining a fluorescent material for molecular imaging with the recombinant albumin prepared in step 3) (step 4).

The present invention also provides a method for the treatment of disease containing the step of administering the said recombinant albumin-drug conjugate to a subject.

The present invention also provides a method for diagnosis of disease comprising the following steps:
1) administering the recombinant albumin-fluorescent material conjugate for molecular imaging to a subject; and
2) obtaining images of disease tissues by irradiating fluorescence.

ADVANTAGEOUS EFFECT

According to the present invention, the recombinant albumin has the increased number of cysteins that can be useful for drug binding at N-terminal and C-terminal along with the 34$^{th}$ residue, so that it not only improves albumin-drug conjugation efficiency for more effective delivery of a large amount of drugs to a target tissue but also facilitates regulation of the number of fused cysteines to control the number of drugs conjugated to each albumin, indicating that this novel recombinant albumin can be used as an excellent drug deliverer with less side effects than the conventional albumin deliverers. In addition, the recombinant albumin of the present invention can be used for the screening of a novel drug and for the non-invasive real-time diagnosis and treatment of disease by combining with a fluorescent material or a contrast agent for molecular imaging.

BRIEF DESCRIPTION OF THE DRAWINGS

The application of the preferred embodiments of the present invention is best understood with reference to the accompanying drawings, wherein.

(1: recombinant albumin fused with poly-cysteine peptide represented by SEQ. ID. NO. 1 at C-terminal;

2; recombinant albumin fused with poly-cysteine peptide represented by SEQ. ID. NO. 1 at N-terminal;

3: recombinant albumin fused with RGD at N-terminal and fused with poly-cysteine peptide represented by SEQ. ID. NO. 1 at C-terminal;

4: recombinant albumin fused with both RGD and poly-cysteine peptide represented by SEQ. ID. NO.1 at N-terminal;

5: recombinant albumin fused with poly-cysteine peptide represented by SEQ. ID. NO.1 respectively at N-terminal and C-terminal;

6: recombinant albumin fused with both RGD and poly-cysteine peptide represented by SEQ. ID. NO.1 at N-terminal and fused with poly-cysteine peptide represented by SEQ. ID. NO.1 at C-terminal;

7: recombinant albumin fused with poly-cysteine peptide represented by SEQ. ID. NO. 2 at C-terminal;

c: human serum albumin; and, m: protein marker)

Figure 4A:
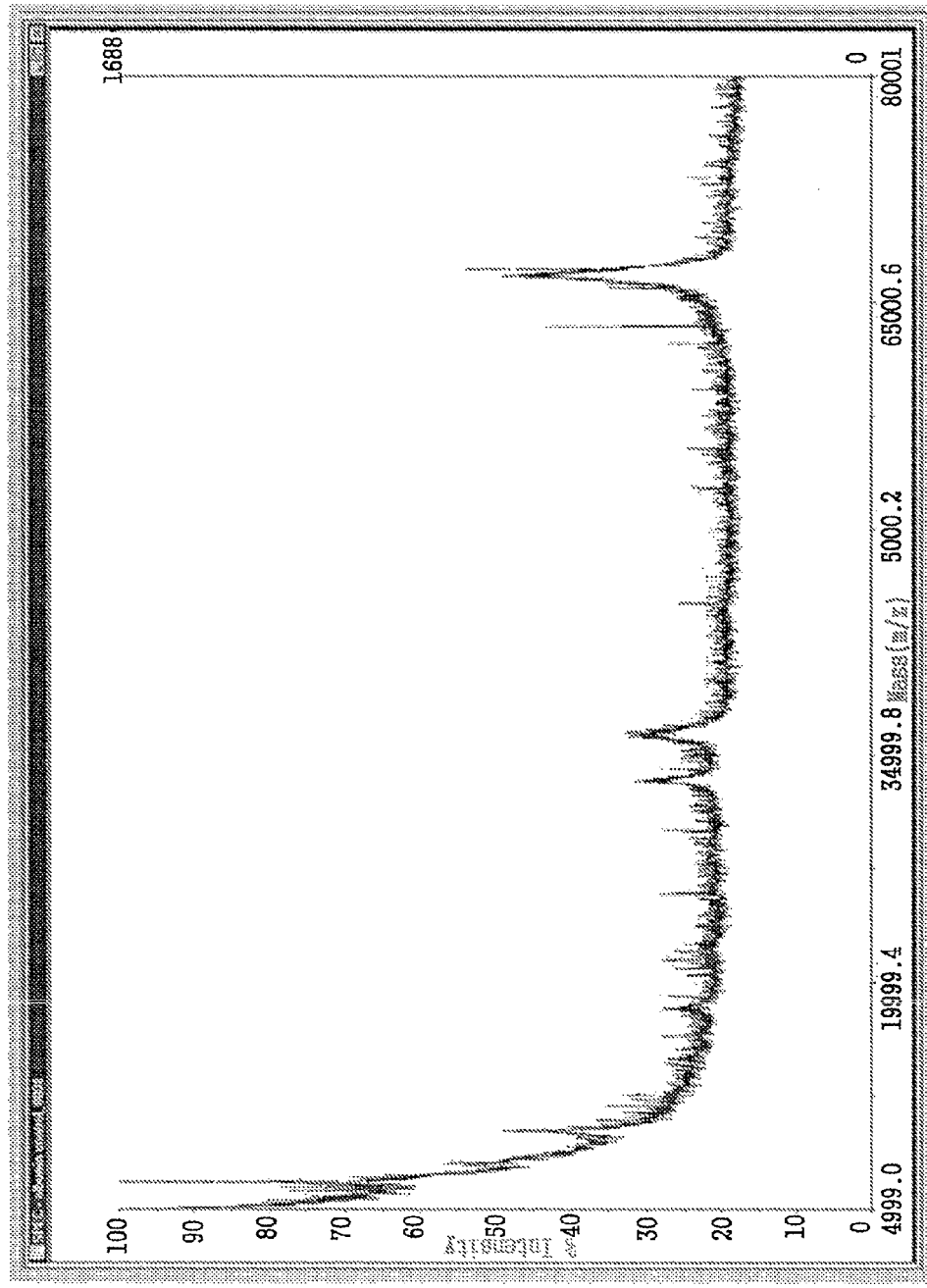
Figure 4B:
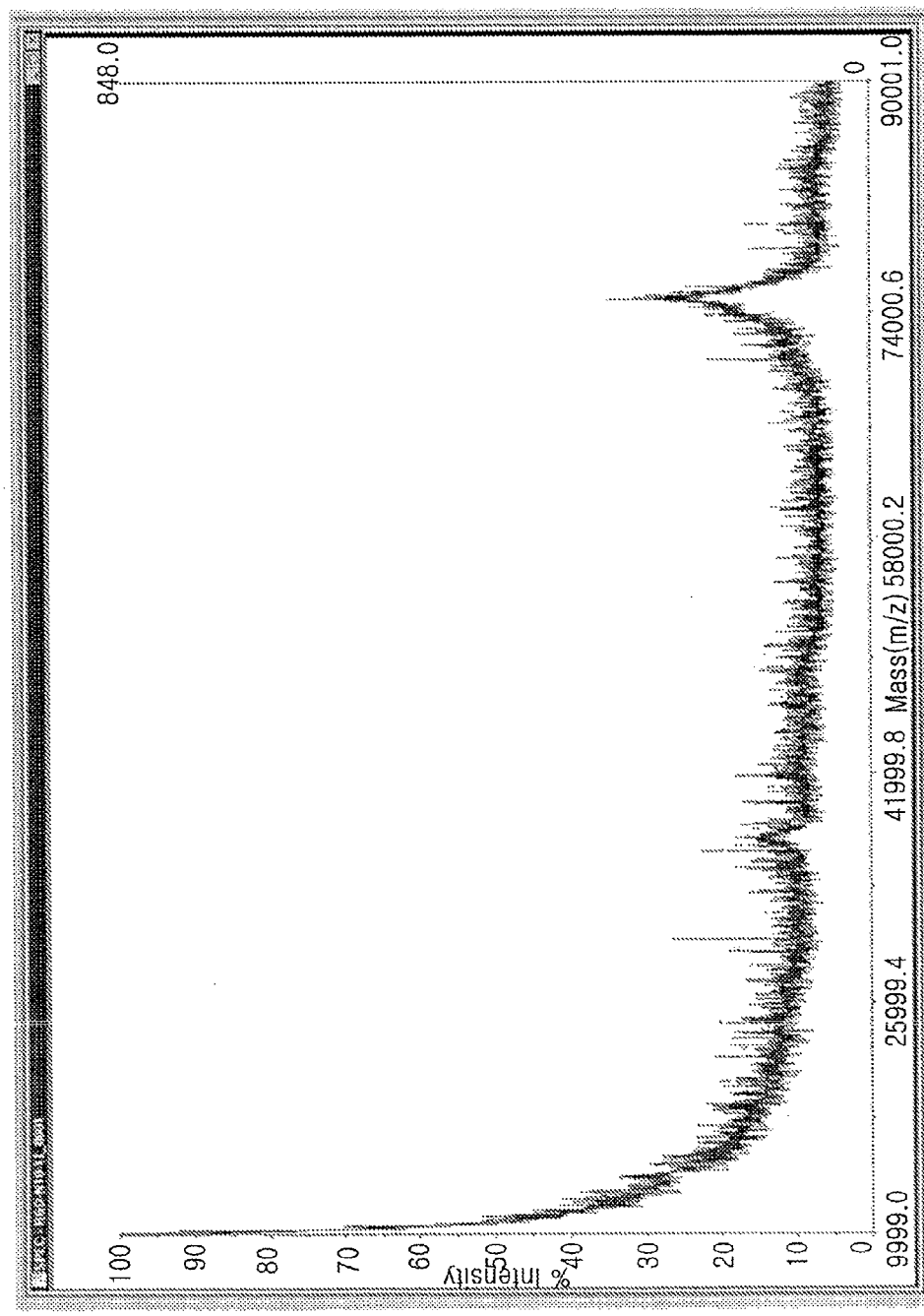

FIG. 4a is a graph illustrating the result of mass analysis of human serum albumin using MALDI-TOF, and FIG. 4b is a graph illustrating the result of mass analysis of the recombinant albumin fused with poly-cysteine peptide containing RGD ligand using MALDI-TOF.

Figure 5:
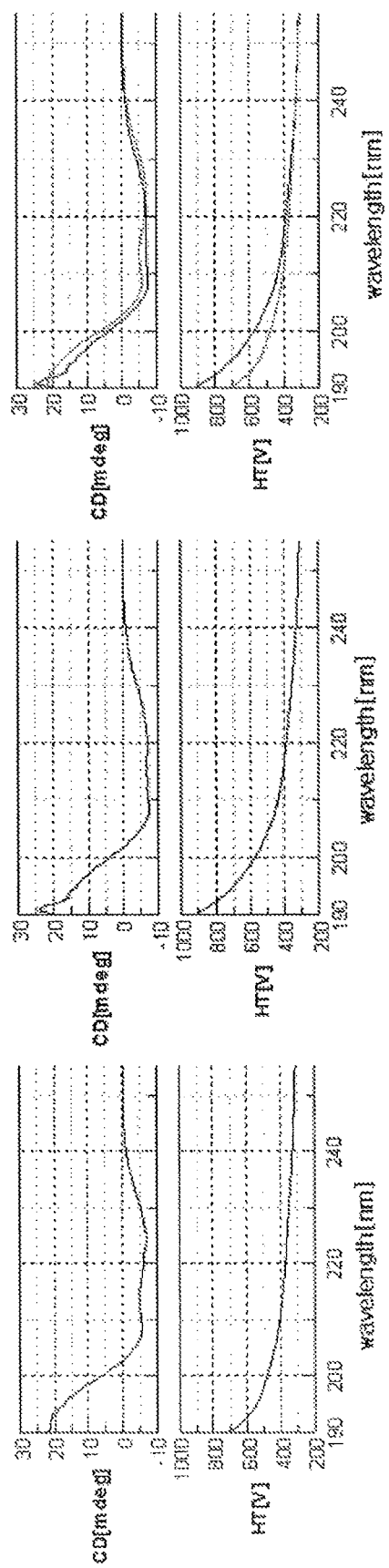

FIG. 5 is a set of graphs illustrating secondary structure and protein folding of human serum albumin and the recombinant albumin fused with poly-cysteine peptide comprising RGF ligand measured by CD (Circular Dichroism).

Figure 6:
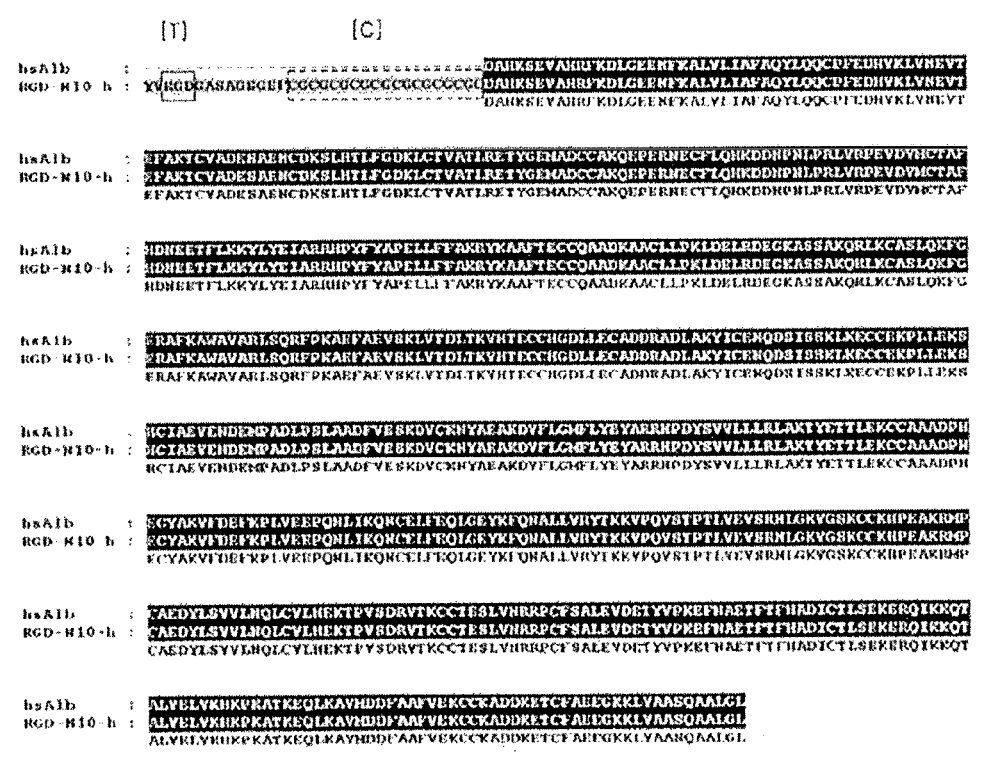

FIG. 6 is a diagram illustrating the result of DNA sequencing of human serum albumin and the recombinant albumin fused with poly-cysteine peptide comprising RGF ligand (hsAlb: human serum albumin, RGD-N10-hsA: recombinant albumin fused with poly-cysteine peptide containing RGD ligand, solid box: RGD ligand, dashed box: poly-cysteine peptide motif).

DESCRIPTION OF THE PREFERRED EMBODIMENTS

Hereinafter, the present invention is described in detail.

The present invention provides a recombinant albumin fused with poly-cysteine peptide.

The said albumin is preferably human albumin, its fragments or its variants, but not always limited thereto.

Albumin is endogenous and it has excellent biocompatibility, biostability, and high blood distribution, so that it can be continuously accumulated in cancer tissues for long enough.

The said poly-cysteine peptide is preferably fused with either one or both ends of albumin, but not always limited thereto.

The poly-cysteine peptide preferably contains 1-100 cysteine residues, but not always limited thereto.

The poly-cysteine peptide contains more than 80% of cysteine residues, preferably more than 60% of cysteine residues, more preferably more than 40% of cysteine residues, and most preferably more than 20% of cysteine residues in its peptide sequence, but not always limited thereto.

The sequence of the poly-cysteine peptide is not limited to a specific sequence, and the ratio of cysteine to peptide is not limited either. Preferably, the poly-cysteine peptide has the sequence represented by SEQ. ID. NO. 1 or SEQ. ID. NO. 2, but not always limited thereto.

SEQ. ID. NO. 1:   [ CGCGCGCGCGCGCGCGCGCG ]

SEQ. ID. NO.      [ CSCSCSCSCS ]

Thiol group of cysteine in the poly-cysteine peptide is easily reacted with maleimide reaction group in a drug or a fluorescent material, resulting in stable carbon-sulfur bond.

The recombinant albumin of the present invention preferably contains an additional linker peptide, but not always limited thereto.

The linker peptide is preferably inserted between both ends of albumin and poly-cysteine peptide, but not always limited thereto. The linker peptide is preferably composed of 1-100 amino acids, but not always limited thereto.

The sequence of the linker peptide is not limited to a specific sequence, but simple structured amino acids with short amino acid side chain or without amino acid side chain is preferred. The sequence is more preferably composed of glycine, serine, and alanine, but not always limited thereto. The sequence is also preferably the one represented by SEQ. ID. NO. 3, but not always limited thereto.

SEQ. ID. NO. 3:   [ GSGAGSGA ]

The linker peptide acts as a linker connecting poly-cysteine peptide to albumin during genetic recombination process.

The recombinant albumin of the present invention preferably contains a target tissue recognition ligand, but not always limited thereto.

The target tissue recognition ligand is conjugated to one or both ends of poly-cysteine peptide by protein chain linking or covalent, bonding, or conjugated to a residue of poly-cysteine peptide based on genetic recombination technique, but not always limited thereto.

The target tissue recognition ligand is selectively binding to a receptor over-expressed in a specific target tissue such as cancer cells. Thus, when it is added to the recombinant albumin of the present invention, it endows the recombinant albumin specific target (such as cancer cells) oriented function. The target recognition ligand of the present invention includes any material that can be selectively recognized by a target tissue.

The target tissue recognition ligand is preferably selected from the group consisting of peptides containing RGD (Arginine-Glycine-Aspartic acid), aptamer, and folate, but not always limited thereto.

The peptide containing RGC used as a target recognition ligand is the one that has one or more repetitive motifs binding to the receptor of vascular endothelial growth factor (VEGF), and is capable of endowing target-orientation toward cancer cells.

The present invention also provides a recombinant albumin-drug conjugate produced by combining a drug with the said recombinant albumin and a pharmaceutical composition comprising the recombinant albumin-drug conjugate.

The drug herein includes every drug that can be successfully delivered to a target, tissue by being conjugated with thiol group of poly-cysteine peptide. Preferably, it is an anti-cancer agent, siRNA or a therapeutic agent for intractable disease, and more preferably it is selected from the group consisting of Docetaxel, cis-platin, camptothecin, paclitaxel, Tamoxifen, Anasterozole, Gleevec, 5-FU, Floxuridine, Leuprolide, Flutamide, Zoledronate, Doxorubicin, Vincristine, Gemcitabine, Streptozocin, Carboplatin, Topotecan, Belotecan, Irinotecan, Vinorelbine, hydroxyurea, Valrubicin, retinoic acid, Methotrexate, Meclorethamine, Chlorambucil, Busulfan, Doxifluridine, Vinblastin, Mitomycin, Prednisone, Testosterone, Mitoxantron, aspirin, salicylates, ibuprofen, naproxen, fenoprofen, indomethacin, phenyltazone, cyclophosphamide, mechlorethamine, dexamethasone, prednisolone, celecoxib, valdecoxib, nimesulide, cortisone and corticosteroid, but not always limited thereto.

The method of combining the drug with thiol group of poly-cysteine peptide is exemplified by the conjugation using maleimide reaction group, the conjugation using idoacetyl reaction group, or the conjugation using pyridyl disulfide reaction group, but not always limited thereto.

When the recombinant albumin-drug conjugate of the present invention is used, biostability can be regulated based on the interaction between albumin and the drug fused with poly-cysteine peptide by regulating the length of a linker peptide connecting poly-cysteine peptide and albumin.

The present invention also provides a recombinant albumin-fluorescent material conjugate for molecular imaging produced by combining a fluorescent material for molecular imaging with the said recombinant albumin and a composition for disease diagnosis comprising the said recombinant albumin-fluorescent material for molecular imaging.

The fluorescent material for molecular imaging herein is conjugated to one or both ends of poly-cysteine peptide by protein chain linking or covalent bonding, or conjugated to a residue of poly-cysteine peptide based on genetic recombination technique, but not always limited thereto.

The fluorescent material for molecular imaging herein includes every material that can irradiate fluorescence, and more preferably the one that can irradiate red or near-infrared fluorescence, and most preferably the one that has high quantum yield, but not always limited thereto.

The fluorescent material for molecular imaging is preferably a fluorescent material, a fluorescent protein, or any other material for imaging that has the bond of thiol group of poly-cysteine peptide and maleimide reaction group, but not always limited thereto.

The fluorescent material having the bond of thiol group and maleimide reaction group is exemplified by fluorescein, BODYPY, Tetramethylrhodamine, Alexa, Cyanine, allopicocyanine and their derivatives, but not always limited thereto. Among these fluorescent materials, cyanine and Alexa release and absorb near-infrared ray, indicating that intervention or absorption into cells, blood and biotissues becomes minimized, which are preferred.

The fluorescent protein herein is preferably exemplified by Dronpa protein, EGFP, red fluorescent protein (DsRFP), Cy5.5 and other fluorescent proteins, but not always limited thereto.

Other materials for imaging that can be included in this invention are preferably iron oxide, radio-isotope, etc, but not always limited thereto. And these materials can be applied to imaging systems such as MR and PET.

The recombinant albumin of the present invention can effectively deliver a drug or a fluorescent material for molecular imaging to a target cell or tissue. Therefore, it is suitable for multi-purpose utilization including drug delivery system, cellular imaging, specific tissue imaging, etc, and can be applicable in vivo and in vitro as well.

The recombinant albumin of the present invention is preferably represented by one of the following <Formula 1>-<Formula 4>, but not always limited thereto:

[T]-[C]-[L]-[A]-[L]-[C]-[D]  <Formula 1>

[T]-[C]-[L]-[A]-[L]-[C]-[P]  <Formula 2>

[T]-[C]-[L]-[A]-[L]-[C]-[D]-[P]  <Formula 3>

[T]-[C]-[L]-[A]-[L]-[C]-[P]-[D]  <Formula 4>

In the above formulas, T indicates a target tissue recognition ligand, C indicates poly-cysteine peptide, L indicates a linker peptide, A indicates albumin, D indicates a drug, and P indicates a fluorescent material for molecular imaging.

Figure 1:
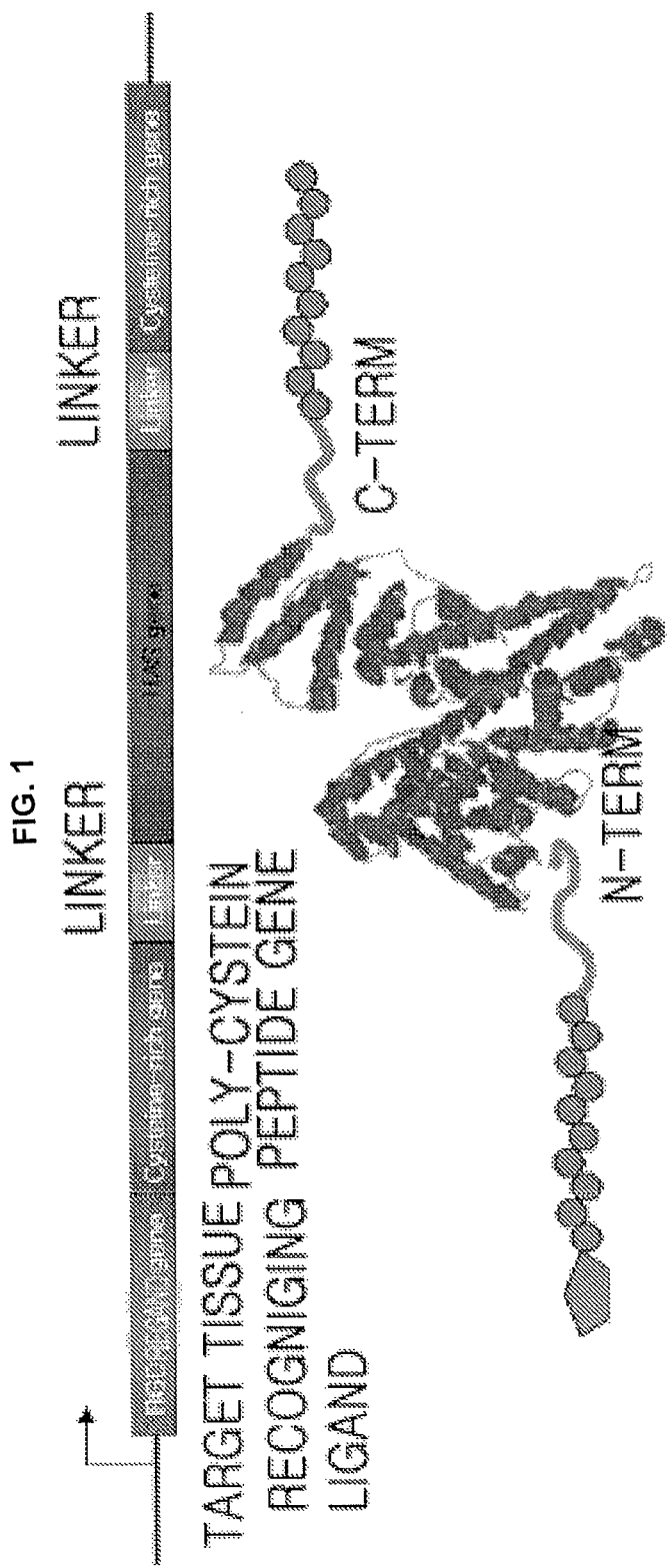
FIG. 1 is a schematic diagram illustrating RGD (Arginine-Glycine-Aspartic acid) peptide gene, poly-cysteine peptide gene, linker peptide gene, recombinant albumin gene and a recombinant albumin fused with poly-cysteine peptide expressed as one amino acid chain therefrom, based on genetic recombination technique.

As shown in FIG. 1, the recombinant albumin of the present invention can be constructed by using RGD peptide gene, poly-cysteine peptide gene, linker peptide gene, and recombinant albumin gene, that is, from those genes a recombinant albumin expressed as one amino acid chain can be obtained.

The obtained recombinant albumin contains multiple cysteines which are the locations for drug binding, so that the albumin-drug conjugation efficiency can be increased and accordingly a large amount of drug can be effectively delivered to target tissues. While preparing the recombinant gene, the number of cysteines can be regulated, by which the number of drugs that are supposed to be conjugated to each unit albumin can also be regulated.

The obtained recombinant albumin is separated and purified by ion exchange chromatography and size-exclusion gel filtration chromatography. Molecular weight of the recombinant albumin is confirmed by denatured SDS-PAGE and mass spectrometry (see FIG. 2).

Figure 3:
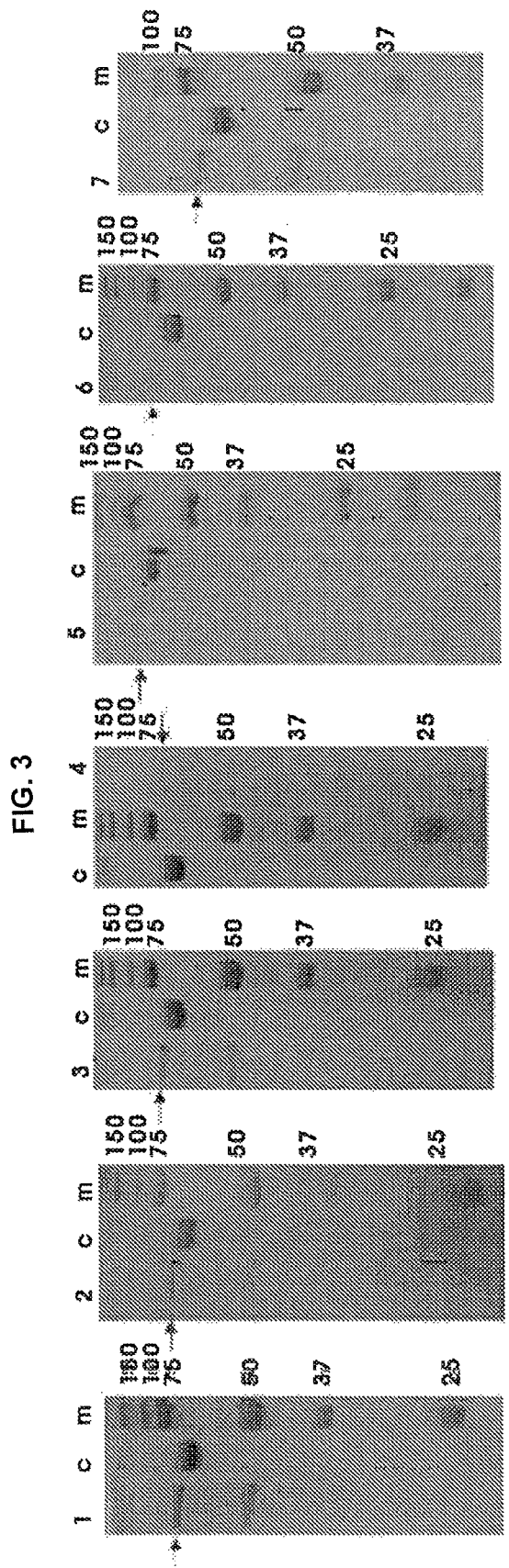
FIG. 3 is a set of photographs illustrating the fusion of poly-cysteine peptide with either one or both ends of albumin (N-terminal and C-terminal), resulting in different types of recombinant albumins expressed in *Pichia pastoris*.

As shown in FIG. 3, poly-cysteine peptide is fused alone to either N-terminal or C-terminal of albumin or to both ends of it, resulting in different kinds of recombinant albumins, which can be found in *Pichia pastoris*.

From the mass spectrometry, it was confirmed that human serum albumin and the recombinant albumin fused with poly-cysteine peptide had 67.2 kDa and 74.8 kDa, respectively, suggesting that there is 7.6 kDa difference in molecular weight between the two (see FIGS. 4a and 4b). The recombinant albumin fused with poly-cysteine peptide showed the same protein folding as human serum albumin (see FIG. 5).

Therefore, the recombinant albumin of the present invention dose not affect the 3 dimensional structure and functions of albumin and at the same time maintains its unique physical and chemical properties. This suggests that the recombinant albumin keeps the functions for effective drug delivery in addition to the advantageous characteristics such as high accumulation in target tissues such as cancer and rheumatoid arthritis tissues, low invasiveness in normal tissues, low toxicity, capability of binding with various drugs and drug release in target tissues, preferable biodegradation time for excellent stability, excellent biocompatibility, and preferable solubility of fused drug, etc. The recombinant albumin of the present invention maintains the excellent functions of albumin, particularly functions for drug delivery, and at the same time reduced side effects which are common in the conventional albumin, so that it can be used as an excellent drug deliverer.

DNA sequencing with the recombinant albumin expressed in *Pichia pastoris* was performed. As a result, it was confirmed to have the same albumin region and RGD ligand peptide and poly-cysteine peptide motif were expressed as expected (see FIG. 6). Therefore, it was confirmed that the sequence and the length of poly-cysteine peptide to be fused with albumin by genetic recombination could be regulated.

The recombinant albumin of the present invention can be fused with siRNA to produce a disulfide bond conjugate of siRNA-recombinant albumin fused with poly-cysteine peptide.

As explained hereinbefore, the recombinant albumin fused with poly-cysteine peptide of the present invention facilitates modification and control of poly-cysteine peptide, a linker peptide, a drug, a fluorescent material for molecular imaging, and a target recognition ligand, suggesting that it is easy to control specific drug/albumin ratio, specific types of drugs, fluorescence of specific wave length band, and target specific recognition ligand. Therefore, carriers based on different albumins can be designed with the recombinant albumin of the invention.

The present invention provides a polynucleotide encoding the said recombinant albumin, an expression vector introduced with the said polynucleotide and a transformant transfected with the said expression vector.

The present invention also provides a method for preparing the said recombinant albumin comprising the following steps:
1) constructing the said expression vector;
2) preparing the said transformant by transfecting a host cell with the expression vector constructed in step 1); and
3) obtaining the recombinant albumin fused with poly-cysteine peptide from the transformant prepared in step 2).

In the above method, the expression vector step 1) has preferably the structure that poly-cysteine peptide gene is fused with one or both ends of albumin gene, but not always limited thereto.

In the above method, the host cell of step 2) is preferably *Pichia pastoris*, but not always limited thereto.

In the above method, the additional step for separation and purification or identification of the recombinant albumin prepared in step 3) can be included.

The present invention also provides a method for preparing a recombinant albumin-drug conjugate containing the additional step (step 4) of obtaining a recombinant albumin-drug conjugate by combining a drug with the recombinant albumin obtained in step 3).

The present invention also provides a method for preparing a recombinant albumin-fluorescent material conjugate for molecular imaging comprising the additional step (step 4) of obtaining a recombinant albumin-fluorescent material conjugate for molecular imaging by combining a fluorescent material for molecular imaging with the recombinant albumin prepared in step 3).

The present invention also provides a method for the treatment of disease containing the step of administering the said recombinant albumin-drug conjugate to a subject.

The recombinant albumin-drug conjugate of the present invention can be used for the diagnosis and treatment of various diseases including cancer, osteoarthritis, rheumatoid arthritis, dementia, autoimmune disease, and stroke.

The cancer herein is preferably squamous cell carcinoma, uterine cancer, cervical cancer, prostate cancer, head and neck cancer, pancreatic cancer, brain tumor, breast cancer, liver cancer, skin cancer, esophageal cancer, testicular cancer, kidney cancer, colon cancer, rectal cancer, stomach cancer, bladder cancer, ovarian cancer, cholangioma, or gallbladder cancer, but not always limited thereto.

The present invention also provides a method for the diagnosis of disease comprising the following steps:
1) administering the recombinant albumin-fluorescent material conjugate for molecular imaging to a subject; and
2) obtaining images of disease tissues by irradiating fluorescence.

The recombinant albumin of the present invention can be used to inhibit overexpression of a target gene by delivering siRNA to a target gene in various types of cancer cells and used for the screening of a novel drug having the said mechanism.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

EXAMPLE 1

Construction of Expression Vector for Recombinant Albumin Fused with Poly-Cysteine Peptide Genetic recombination technique was used to insert poly-cysteine peptide and a linker peptide into albumin. The expression vector used herein was pUIC9 which is the expression vector of *Pichia pastoris*. The sequence inducing expressions of poly-cysteine peptide and a linker peptide was inserted by using a restriction enzyme.

The inserted poly-cysteine peptide amino acid sequence was the one represented by SEQ. ID. NO. 1 or NO. 2. The poly-cysteine peptide was fused with either N-terminal or C-terminal of albumin or both ends simultaneously.

SEQ. ID. NO. 1:     [ CGCGCGCGCGCGCGCGCGCG ]

SEQ. ID. NO. 2:     [ CSCSCSCSCS ]

The linker peptide was the peptide represented by SEQ. ID. NO. 3, and glycine, serine, and alanine were mainly used.

SEQ. ID. NO. 3:     [ GSGAGSGA ]

To endow target-orientation toward cancer cells, RGD peptide that is conjugated with a receptor over-expressed in cancer cells was fused in front of the poly-cysteine peptide sequence.

The sequence encoding poly-cysteine peptide, the sequence encoding a linker peptide and RGD peptide gene in pUIC9 expression vector are illustrated in FIG. 1.

EXAMPLE 2

Mass-Expression, Separation and Purification of Recombinant Albumin Fused with Poly-Cysteine Following experiment was performed to insert a recombinant albumin fused with poly-cysteine comprising RGD into HIS4 region.

The expression vector was digested with SalI, followed by purification with column. Competent cells (40 μl) were transformed with 100 ng of the obtained DNA by electrophoration. HIS+phenotype producing histidine was selected from HIS (−) media.

Among the 50 transformants obtained above, Mut+ phenotypes well growing in both MD and MM were selected by replica method using a control strain (GS115 Albumin: HIS+ Muts). Genomic DNA was separated from 8 HIS+Mut+ strains, followed by PCR to confirm the insertion. Strains confirmed by all of the above three methods were selected and used for expression test.

Seed culture (30□, 180-200 rpm, 12 hours) was performed in BMGY culture flask (BMGY 20 ml/250 ml baffled flask). The cells were harvested and inoculated in BMMY culture flask (BMMY 50 ml/250 ml baffled flask), followed by small scale expression test.

Methanol induction was performed at the concentration of 0.5% every 12 hours. While culturing 0-96 hours, optimum culture conditions were searched. The conditions are as follows.

[HIS(−) medium: YBB 6.7 g, HIS DO supplement 0.77 g, glucose 20 g, agar 15 g]

[MM medium: YNB 13.4 g, biotin 4×10-5%, methanol 0.5%, agar 15 g]

[MD medium: YNB 13.4 g, biotin 4×10-5%, glucose 20 g, agar 15 g]

[BMGY medium: 0.1 M potassium phosphate buffer (pH 6.0), YNB 13.4 g, yeast extract 10 g, bactopeptone 20 g, Glycerol 10 g, biotin 4×10-5%]

[BMMY medium: 0.1M potassium phosphate buffer (pH 6.0), YNB 13.4 g, yeast extract 10 g, bactopeptone 20 g, methanol 0.5%, biotin 4×10-5%]

Media were collected and concentrated. Proteins were separated and purified by ion exchange chromatography and size-exclusion gel filtration chromatography. Molecular weight of the purified protein was confirmed by denatured SDS-PAGE and MALD-TOF. The results are shown in FIG. 2-FIG. 4.

Figure 2:
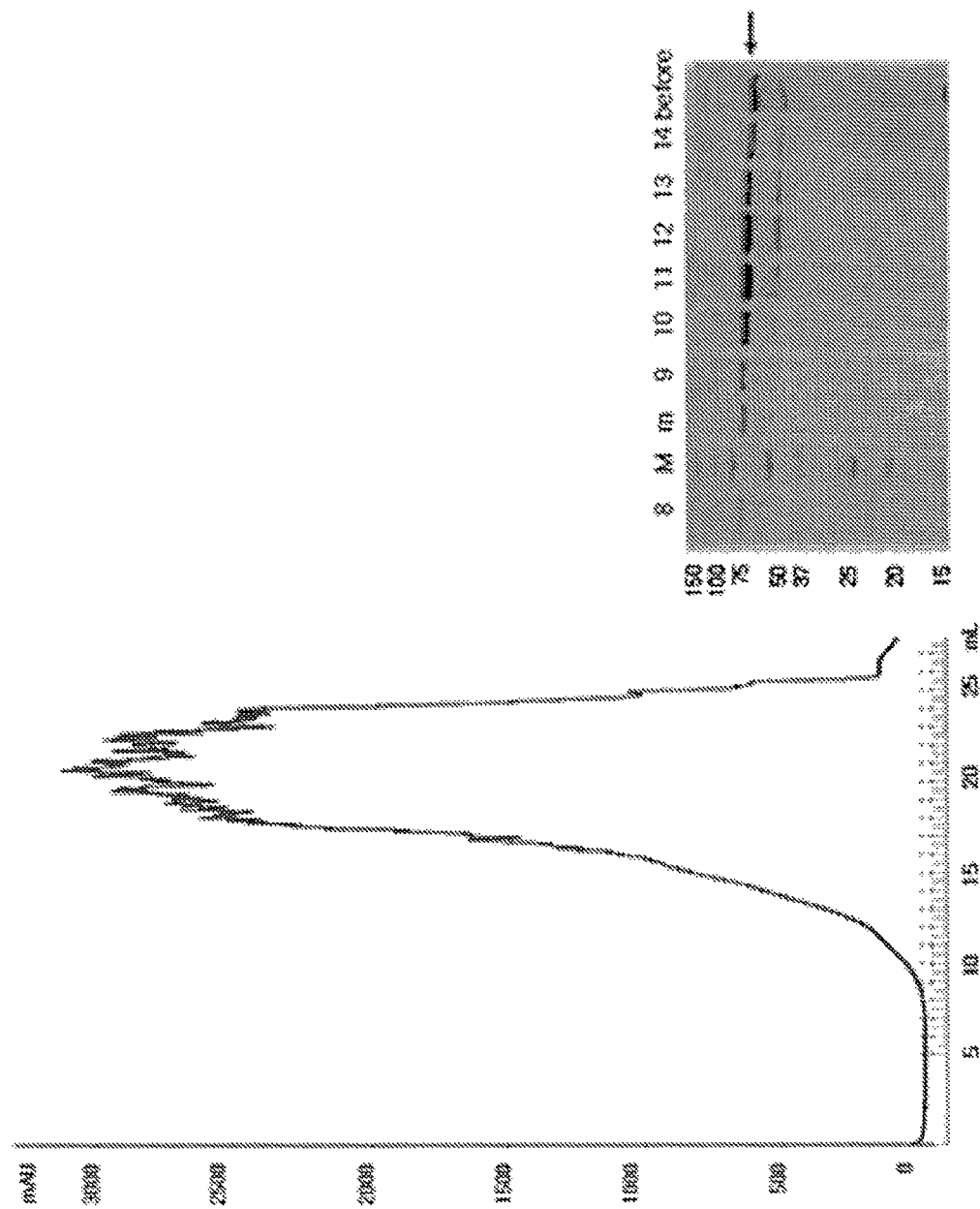
FIG. 2 is a diagram illustrating molecular weight of the recombinant albumin fused with poly-cysteine peptide of the present invention, confirmed by denatured SDS-PAGE and MALD-TOF (M: protein marker, m: human serum albumin, before: sample before injection, 8-14: eluted fractions).

As shown in FIG. 2, molecular weight of the recombinant albumin fused with poly-cysteine peptide was confirmed by denatured SDS-PAGE and MALD-TOF (M: protein marker, m: human serum albumin, before: sample before injection, 8-14: eluted fractions).

As shown in FIG. 3, different types of recombinant albumins, fused with poly-cysteine peptide either at N-terminal or C-terminal of albumin or both ends of albumin, were expressed in *Pichia pastoris*.

To investigate the molecular weights of the conventional human serum albumin and the recombinant albumin fused with poly-cysteine peptide comprising RGD ligand, mass analysis was performed by using MALDI-TOF (FIG. 4a and FIG. 4b). As shown in FIG. 4a and FIG. 4b, human serum albumin had 67.2 kDa and the recombinant albumin fused with poly-cysteine peptide of the present invention had 74.8 kDa, indicating there was 7.6 kDa difference in molecular weight between the two.

To investigate whether secondary structure and protein folding were changed in the recombinant albumin fused with poly-cysteine comprising RGD ligand, protein folding was measured by Circular Dichroism (CD) (FIG. 5). As shown in FIG. 5, the same protein folding was observed in the recombinant albumin fused with poly-cysteine and in human serum albumin.

DNA sequencing was performed with the recombinant albumin expressed in *Pichia pastoris* (FIG. 6). As a result, albumin region of the recombinant albumin was same as that of the conventional albumin, and RGD ligand peptide motif and poly-cysteine peptide motif were expressed as designed.

The following sequence represented by SEQ. ID. NO. 4 is the amino acid sequence of the recombinant sequence represented by SEQ. ID. NO. 5 is the amino acid sequence of human serum albumin, and the sequence represented by SEQ. ID. NO. 6 is the poly-nucleotide sequence encoding the recombinant albumin.

```
SEQ. ID. NO. 4:
YVRGDGASAGSGEFCGCGCGCGCGCGCGCGCGCDAHKSEVAHRFKDLGE

ENFKALVLIAFAQYLQQCPFEDHVKLVNEVTEFAKTCVADESAENCDKS

LHTLFGDKLCTVATLRETYGEMADCCAKQEPERNECFLQHKDDNPNLPR

LVRPEVDVMCTAFHDNEETFLKKYLYEIARRHPYFYAPELLFFAKRYKA

AFTECCQAADKAACLLPKLDELRDEGKASSAKQRLKCASLQKFGERAFK

AWAVARLSQRFPKAEFAEVSKLVTDLTKVHTECCHGDLLECADDRADLA

KYICENQDSISSKLKECCEKPLLEKSHCIAEVENDEMPADLPSLAADFV

ESKDVCKNYAEAKDVFLGMFLYEYARRHPDYSVVLLLRLAKTYETTLEK

CCAAADPHECYAKVFDEFKPLVEEPQNLIKQNCELFEQLGEYKFQNALL

VRYTKKVPQVSTPTLVEVSRNLGKVGSKCCKHPEAKRMPCAEDYLSVVL

NQLCVLHEKTPVSDRVTKCCTESLVNRRPCFSALEVDETYVPKEFNAET

FTFHADICTLSEKERQIKKQTALVELVKHKPKATKEQLKAVMDDFAAFV

EKCCKADDKETCFAEEGKKLVAASQAALGL

SEQ. ID. NO. 5:
DAHKSEVAHRFKDLGEENFKALVLIAFAQYLQQCPFEDHVKLVNEVTEF

AKTCVADESAENCDKSLHTLFGDKLCTVATLRETYGEMADCCAKQEPER

NECFLQHKDDNPNLPRLVRPEVDVMCTAFHDNEETFLKKYLYEIARRHP

YFYAPELLFFAKRYKAAFTECCQAADKAACLLPKLDELRDEGKASSAKQ

RLKCASLQKFGERAFKAWAVARLSQRFPKAEFAEVSKLVTDLTKVHTEC

CHGDLLECADDRADLAKYICENQDSISSKLKECCEKPLLEKSHCIAEVE

NDEMPADLPSLAADFVESKDVCKNYAEAKDVFLGMFLYEYARRHPDYSV

VLLLRLAKTYETTLEKCCAAADPHECYAKVFDEFKPLVEEPQNLIKQNC

ELFEQLGEYKFQNALLVRYTKKVPQVSTPTLVEVSRNLGKVGSKCCKHP

EAKRMPCAEDYLSVVLNQLCVLHEKTPVSDRVTKCCTESLVNRRPCFSA

LEVDETYVPKEFNAETFTFHADICTLSEKERQIKKQTALVELVKHKPKA

TKEQLKAVMDDFAAFVEKCCKADDKETCFAEEGKKLVAASQAALGL

SEQ. ID. NO. 6:
tacgtaagaggtgatggtgcttctgctggttctggtgaattctgtggat gtggttgtggttgtggatgtggttgtggatgtggttgtggatgtggttg tgatgcacacaagagtgaggttgctcatcggtttaaagatttgggagaa gaaaatttcaaagccttggtgttgattgcctttgctcagtatcttcagc agtgtccatttgaagatcatgtaaaattagtgaatgaagtaactgaatt tgcaaaaacatgtgttgctgatgagtcagctgaaaattgtgacaaatca cttcatacccttttttggagacaaattatgcacagttgcaactcttcgtg aaacctatggtgaaatggctgactgctgtgcaaaacaagaacctgagag aaatgaatgcttcttgcaacacaaagatgacaacccaaacctccccga ttggtgagaccagaggttgatgtgatgtgcactgcttttcatgacaatg aagagacatttttgaaaaaatacttatatgaaattgccagaagacatcc ttactttatgccccggaactccttttctttgctaaaaggtataaagct gcttttacagaatgttgccaagctgctgataaagctgcctgcctgttgc caaagctcgatgaacttcgggatgaagggaaggcttcgtctgccaaaca
```

-continued

```
gagactcaagtgtgccagtctccaaaaatttggagaaagagctttcaaa gcatgggcagtagctcgtctgagccagagatttcccaaagctgagtttg cagaagtttccaagttagtgacagatcttaccaaagtccacacggaatg ctgccatggagatctgcttgaatgtgctgatgacagggcggaccttgcc aagtatatctgtgaaaatcaagattcgatctccagtaaactgaaggaat gctgtgaaaaacctctgttggaaaaatcccactgcattgccgaagtgga aaatgatgagatgcctgctgacttgccttcattagctgctgattttgtt gaaagtaaggatgtttgcaaaaactatgctgaggcaaaggatgtcttcc tgggcatgtttttgtatgaatatgcaagaaggcatcctgattactctgt cgtgctgctgctgagacttgccaagacatatgaaaccactctagagaag tgctgtgccgctgcagatcctcatgaatgctatgccaaagtgttcgatg aatttaaacctcttgtggaagagcctcagaatttaatcaaacaaaattg tgagcttttgagcagcttggagagtacaaattccagaatgcgctatta gttcgttacaccaagaaagtaccccaagtgtcaactccaactcttgtag aggtctcaagaaacctaggaaaagtgggcagcaaatgttgtaaacatcc tgaagcaaaaagaatgccctgtgcagaagactatctatccgtggtcctg aaccagttatgtgtgttgcatgagaaaacgccagtaagtgacagagtca ccaaatgctgcacagaatccttggtgaacaggcgaccatgcttttcagc tctggaagtcgatgaaacatacgttcccaaagagtttaatgctgaaaca ttcaccttccatgcagatatatgcacactttctgagaaggagagacaaa tcaagaaacaaactgcacttgttgagctcgtgaaacacaagcccaaggc aacaaaagagcaactgaaagctgttatggatgatttcgcagcttttgta
```

-continued

```
gagaagtgctgcaaggctgacgataaggagacctgctttgccgaggagg gtaaaaaacttgttgctgcaagtcaagctgccttaggcttataa
```

EXAMPLE 3

Method for Conjugation of Drug with Recombinant Albumin Fused with Poly-Cysteine Peptide A recombinant albumin-drug conjugate was prepared by chemical binding of a drug with a recombinant albumin fused with poly-cysteine. The drug herein was an anticancer agent, siRNA or a therapeutic agent for intractable disease.

In the case of using siRNA as a drug to be fused, 5'-end of siRNA was modified with amine and combined with poly-cysteine residues at N-terminal and C-terminal of a recombinant albumin by thiol binding. At this time, siRNA (250 µg) modified with amine dissolved in PBS-EDTA (pH 7.4) was reacted with sulfo-LC-SPDP(sulfo-succinimidyl 6-[3-(2-pyridyldithio)-propionamido]hexanoate) at room temperature for 2 hours, resulting in pyridyldithiol-activated siRNA. The remaining SPDP and byproducts were eliminated by using desalting column.

The prepared siRNA was mixed with the recombinant albumin fused with poly-cysteine peptide via optimization process regulating molecular weight ratio in PBS-EDTA (pH 7.4), followed by reaction at room temperature for 12 hours to give a disulfide bond conjugate of siRNA-recombinant albumin fused with poly-cysteine peptide.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

---

What is claimed is:

1. A recombinant albumin fused with a poly-cysteine peptide, wherein the poly-cysteine peptide has the sequence represented by SEQ. ID. NO. 1 or NO. 2.

2. The recombinant albumin according to claim 1, wherein the albumin is human albumin represented by SEQ. ID. NO. 5.

3. The recombinant albumin according to claim 1, wherein the poly-cysteine peptide is fused with the N-terminus of the albumin.

4. The recombinant albumin according to claim 1, wherein a linker peptide is additionally included between albumin and the poly-cysteine peptide.

5. The recombinant albumin according to claim 4, wherein the linker peptide has the sequence represented by SEQ. ID. NO. 3.

6. The recombinant albumin according to claim 3, wherein a target tissue recognition ligand is covalently conjugated to the N-terminus of the poly-cysteine peptide.

7. The recombinant albumin-drug conjugates prepared by combining a drug with the recombinant albumin of claim 6.

8. The recombinant albumin-drug conjugate according to claim 7, wherein the drug is an anticancer agent, siRNA or a therapeutic agent.

9. A pharmaceutical composition comprising the recombinant albumin-drug conjugate of claim 7.

10. The polypeptide of claim 6 further comprising a covalently conjugated fluorophore.

11. A recombinant albumin fused with a poly-cysteine peptide, wherein the resulting polypeptide has the sequence represented by SEQ. ID. NO. 4.

12. A method for in vivo delivery of the conjugates containing the step of administering the recombinant albumin-drug conjugates of claim 7 into a subject.

* * * * *